United States Patent
Scholer et al.

(10) Patent No.: US 6,752,821 B2
(45) Date of Patent: Jun. 22, 2004

(54) ENDOSCOPE PINCERS WITH ROTARY CONNECTOR

(75) Inventors: Uwe Scholer, Hoisdorf (DE); Dido Arnim Zweibruck, Hamburg (DE)

(73) Assignee: Olympus Winter & IBE GmbH, Hamburg (DE)

( * ) Notice: Subject to any disclaimer, the term of this patent is extended or adjusted under 35 U.S.C. 154(b) by 350 days.

(21) Appl. No.: 10/027,031

(22) Filed: Dec. 20, 2001

(65) Prior Publication Data

US 2002/0082640 A1 Jun. 27, 2002

(30) Foreign Application Priority Data

Dec. 22, 2000 (DE) .......................................... 100 64 623

(51) Int. Cl.$^7$ ............................................. A61B 17/28
(52) U.S. Cl. ...................................... 606/205; 606/170
(58) Field of Search ................................ 606/170, 174, 606/180, 175, 205–210, 51, 52; 600/564, 566, 567

(56) References Cited

U.S. PATENT DOCUMENTS

| | | | |
|---|---|---|---|
| 5,174,300 A | * 12/1992 | Bales et al. ................. | 606/170 |
| 5,507,297 A | 4/1996 | Slater et al. | |
| 5,630,818 A | * 5/1997 | Del Rio et al. ............. | 606/180 |
| 5,964,717 A | 10/1999 | Gottlieb et al. | |
| 6,409,728 B1 | * 6/2002 | Ehr et al. .................... | 606/205 |

FOREIGN PATENT DOCUMENTS

| | | |
|---|---|---|
| DE | 25 19 827 | 5/1975 |
| DE | 43 23 584 A1 | 7/1993 |
| DE | 93 17 535.3 | 11/1993 |
| DE | 197 31 884 C1 | 7/1997 |
| DE | 197 47 528 A1 | 10/1997 |
| DE | 298 23 913 U1 | 6/1998 |
| DE | 198 53 305 C1 | 11/1998 |
| EP | 0 688 187 B1 | 3/1994 |
| EP | 0 633 002 A1 | 5/1994 |

* cited by examiner

*Primary Examiner*—Kevin T. Truong
(74) *Attorney, Agent, or Firm*—Rankin, Hill, Porter & Clark LLP

(57) ABSTRACT

Pincers used in endoscope surgery, including a proximal terminal structure and a tube serving as the pincers' stem affixed to the proximal terminal structure. A stationary handle is affixed to the terminal structure. A displaceable handle rests on the stationary handle and is fitted along the tube axis with a swivel seat. A pincers head bears the pincers arms and is detachably and rotatably connected to the distal tube end. An axially displaceable rod drives the pincers arms and is affixed irrotationally to the pincers head. The rod crosses the tube and rests in the swivel seat. The rod is situated in the region of the rotational connection, and exhibits, at least over the engagement zone running the length of its axial displacement, a rotationally asymmetric cross-section. The slider rests in a transverse clearance of the tube, and is fitted with an elongated slot passing the rod. The slot freely passes the proximally situated tube segment exhibiting a maximum-diameter circular cross-section and enclosing the rod's engagement zone in irrotationally locking manner in a gripping zone, which is offset in the sliding direction.

5 Claims, 2 Drawing Sheets

ENDOSCOPE PINCERS WITH ROTARY CONNECTOR

BACKGROUND OF THE INVENTION

1. Field of the Invention

The invention generally relates to endoscope pincers and, more particularly, toward rotary endoscope pincers wherein the term "pincers" concerns an endoscope implement having mutually displaceable arms and may be considered to be similar to scissors.

2. Description of Related Art

Rotary endoscope pincers of the aforementioned-type are characterized by a pincers head that, together with its actuation rod, can be removed from the remnant pincers. This feature entails a detachable but omni directionally firm connection of the pincers head to the distal tube end. However, because the diameter is very narrow, namely only several millimeters, such a connection can be manufactured only with great difficulty.

As a result, pincers of this kind are fitted with a screw or a bayonet connection between the pincers head and the tube. Such a connection provides adequate mechanical strength even under these constricted circumstances. However, such a connection locks only axially and, therefore, for purposes of reliability, further requires a rotary connector. With regard to pincers of this kind, and in view of the restrictions on space, the rotary connector must be situated in the tube's proximal end zone between the proximal end zone and the rod, and also must be detachable to allow dismantling.

The literature, and illustratively the European patent documents 0 688 187 B1 and 0 633 002 A1 and the German patent document 198 55305 C1, discloses several possible designs for the proximal rotary connector between the tube and the rod.

But those designs all entail significant drawbacks. On one hand may be grouped those designs that have an exceedingly complex configuration. On the other hand may be grouped those designs requiring a laborious manual operation to disengage the rotary connector.

SUMMARY OF THE INVENTION

The present invention is directed toward pincers having a rotary connector providing a simplified design that is easy to operate.

An endoscope pincers according to the present invention includes a transversely displaceable slider situated in the tube's proximal end zone and crossed within an elongated slot by the rod. The elongated slot comprises two areas, each of which engage the rod when the slider is located in different slider positions. If, in one slider position, the elongated slot engages by its clearance the rod, then it shall loosely enclose the rod by a clear circular cross-section corresponding to the maximum diameter of the proximal rod segment. Accordingly, the rod then can be rotated relative to the slider and, hence, relative to the tube to be freed thereby for the purpose of releasing the pincers head. In this slider position the rod also can be fully removed from the elongated slot or be reinserted into it. As regards the other slider position, the elongated slot, by means of its gripping zone, will rotationally lock onto an engagement zone of the rod presenting rotational asymmetry, the rod being thereby irrotational or fixed against rotation while being longitudinally displaceable. This design involving a simple slider and a simple rotationally asymmetrical rod zone is exceedingly useful in manufacture.

In further accordance with the present invention, the inventive design offers substantial handling advantages. Particularly, the slider can be displaced in a simple and surveyable manner into a position securing and releasing the rotational connector. No other actuations are required.

The tube may be affixed to the terminal structure. Preferably, however, the tube is detachably affixed in a conventional manner to the terminal structure so as to advantageously constitute pincers that are easily cleaned, namely creating pincers that can be resolved into three parts, that is a pincers head with rod, a tube and a terminal structure.

In further accordance with the present invention, a locking device secures the tube to the terminal structure. The locking device is connected to the slider and thereby eliminates the need to separately actuate the locking device. When driving the slider into the rotationally disengaged position, the tube may be unlocked simultaneously or, alternatively, unlocked when in a third site of extension. In this way the design is simplified and actuation is made easier. If the positions for tube disengagement and rotational unlocking coincide at the slider, then, at this slider position, the pincers can be easily separated into its three components.

In further accordance with the present invention, the tube is rotatably affixed to the terminal structure. Such a design, which may be fitted, for instance, with the tube locking device of the German patent document 198 53 305 C1, is preferred in modern pincers wherein the rotational pincers position relative to the terminal structure can be adjusted arbitrarily.

In further accordance with the present invention, the slider is guided in a rotatably fixed manner in the borehole. This ensures that the slider always assumes its appropriate rotational position wherein the elongated slot may be inserted into the rod.

In further accordance with the present invention, the slider is held by the force of a spring in the engaged position of the gripping zone against the rod. This arrangement ensures that, unless deliberately actuated, the slider keeps the pincers in its locked position.

BRIEF DESCRIPTION OF THE DRAWINGS

These and further features of the invention will be apparent with reference to the following description and drawings, wherein.

DETAILED DESCRIPTION OF THE PREFERRED EMBODIMENTS

Figure 1:
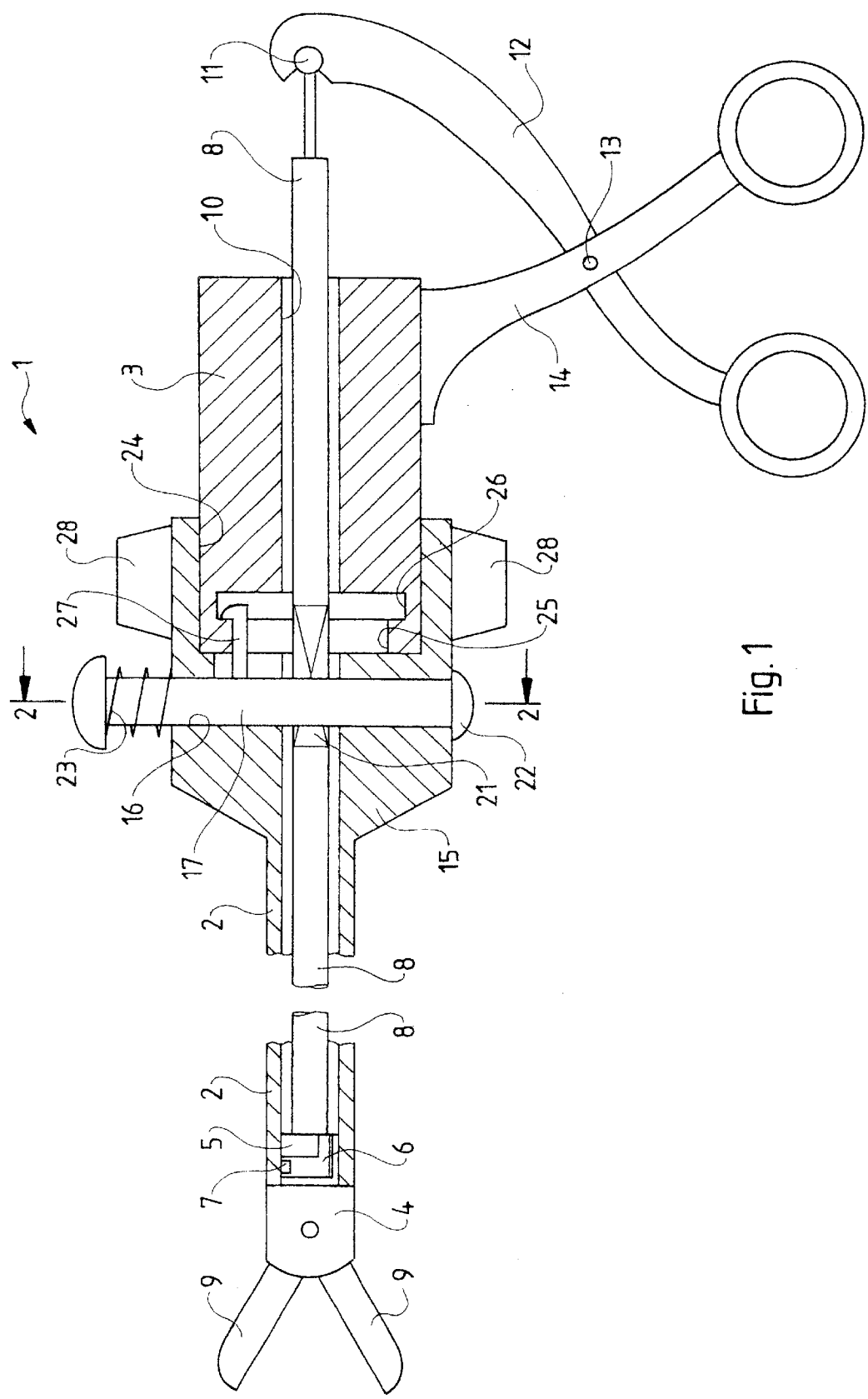
FIG. 1 is an axial section of pincers according to the present invention.

The pincers 1 shown in FIG. 1 is used for endoscope surgery and comprises an elongated, thin stem constituted by a tube 2 and proximally affixed to a pincers terminal structure 3. A pincers head 4 is affixed to a distal end of the tube 2 in the same manner as described in the German patent document 198 53 305 C1. Accordingly, the pincers head is inserted by means of an insert 5 into the tube 2. The insert 5 is fitted on its cylindrical external surface with a bayonet groove 6 which is engaged by an inside pin 7 of the tube 2.

In the shown locked bayonet position, the pincers head 4 is axially secured relative to the tube 2. However, the pincers head 4 may become disengaged during rotational adjustment. Accordingly, additional securing is required against rotation. The same requirement exists if, in an embodiment variation, the shown bayonet lock were replaced by a screw lock.

A rod 8 acts on the pincers head 4 and rests irrotationally but longitudinally displaceably in the pincers head 4. Longitudinal displacement of the rod displaces the pincer arms 9.

In the assembled pincers shown in FIG. 1, the rod 8 runs through the tube 2 and a proximally adjoining borehole 10 of the terminal structure 3. The rod proximally ends behind the terminal structure 3 in the conventional ball 11, which rests detachably in the swivel seat of a displaceable handle 12. This displaceable handle 12 rests at 13 on a stationary handle 14, which is affixed to the terminal structure 3.

In the shown assembled pincers, mutual displacement of the handles 12, 14 longitudinally displaces the rod 8 relative to the tube 2 and will thereby drive the pincers head 4 into opening and closing its arms 9.

As already mentioned above, an additional rotational lock is needed to rotationally secure the bayonet lock 6, 7 of the pincers head 4 to the tube 2. For that purpose, a slider 17 rests inside a clearance 16 running transverse to the axis of the tube 2 at its proximal end zone, which is enlarged at that site into an end segment 15. As shown in the axial side view of FIG. 2, the slider 17 comprises an elongated slot 18 that subtends an upper passage 19 and a lower gripping zone 20.

In the longitudinal zone of the rod 8 situated in the assembled state of FIG. 1 in the region of the slider 17, the rod 8, which elsewhere exhibits, for instance, a circular cross-section, here is fitted with an engagement zone 21 (FIG. 2) of substantially rectangular cross-section. The engagement zone 21 retains its constant cross-section over a length corresponding to its displacement range in which to drive the pincers head 4.

Figure 2:
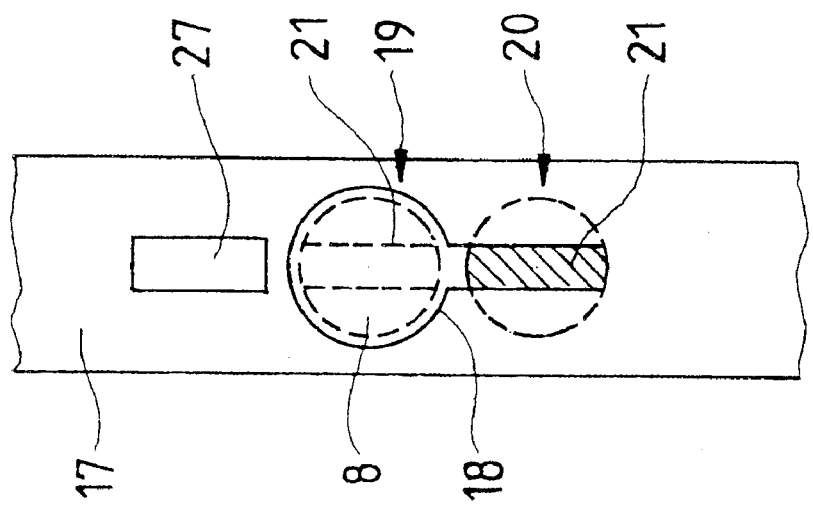
FIG. 2 is a sectional elevation of the slider as seen along line 2—2 of FIG. 1; and, FIG. 3 is a view similar to that of FIG. 2 of a second embodiment of the slider according to the present invention.

For the position of the slider 17 shown in FIG. 2, it is clear that the rod 8 is geometrically locked at its flat engagement zone 21 by the gripping zone 20 of the elongated slot 18. In this manner the rod 8 is irrotationally held in place relative to the slider 17 and, hence, relative to the tube 2 while nevertheless being longitudinally displaceable over the length of the engagement zone 21.

If the slider 17 is displaced enough that the rod 8 now is situated as shown by dashed lines in FIG. 2 in the passage 19 of the elongated slot 18, then the rod will be freely rotatable within the larger clear cross-section of the passage 19, which leaves free a circular cross-section of maximum diameter of the rod 8. In particular, the rod 8 may entirely move through the passage 19 of the slot 18 in the longitudinal direction, including its entire segment situated proximally relative to the slider 17.

As shown by FIG. 1, the slider 17 is kept both by a lower stop 22 and by a closing spring 23 disposed in its upper end position. As such, and with reference to FIG. 2, the engagement zone 21 of the rod 8 is situated in the gripping zone 20 of the elongated slot 18 and the rod 8 is therefore secured against rotation. In this spring-loaded end position of the slider 17, the pincers 1 is secured in its assembled state of FIG. 1. In particular the pincers head 4 is secured against dropping off.

If the pincers must be disassembled for cleaning, finger pressure will depress the slider 17 until the passage 19 of the elongated slot 18 is in the zone of the rod 8. At this point, the pincers head 4 may be seized and rotated to unlock the bayonet connection 6, 7. Also, the pincers head 4 may be fully pulled jointly with the rod 8, the ball 11 being conventionally and automatically released from the displaceable handle 12.

When the pincers are to be reassembled, the rod 8 is inserted from the distal end through the tube 2 until it touches the slider 17. The slider 17 is then depressed so that the passage 19 of the elongated slot 18 aligns with the rod 8 to allow the rod to pass therethrough. To simplify this procedure, the elongated slot 18 may be fitted at its distal aperture with an insertion bevel ensuring that when the rod 8 together with its ball 11 at its proximal comes near the insertion bevel, the slider 17 shall be displaced under slight pressure from the rod until the passage 19 of the elongated slot 18 allows the rod 8 to pass.

In the above description, the tube 2 may be permanently affixed to the terminal structure 3. Desirably, however, the tube 2 will be taken off the terminal structure 3 when cleaning the assembly.

For that purpose, the end segment 15 of the tube 2 is made separate from the terminal structure 3. The end segment 15 can be plugged by means of an end-face borehole 24 onto the terminal structure 3. At its distal end, the terminal structure 3 comprises a terminal borehole 25, which is fitted at its base with an undercut groove 26.

A locking hook 27 is affixed to the slider 17 and, in the shown locking position of the slider 17, engages the groove 26 to lock the tube 2 to the terminal structure 3. If the slider 17 is depressed, the locking hook 27 disengages from the undercut groove 26 and, thus, may be removed with the tube 2.

Accordingly, when the slider 17 is depressed, the tube 2 is simultaneously disengaged from the terminal structure 3 and the rotational connection between the rod 8 and the tube 2 is disengaged. In another design the configuration, however, may be such that, at different insertion depths of the slider 17, illustratively, first only the locking hook 27 is disengaged and then only the rotational mechanical interlock with the rod 8. For that purpose, and for instance in the manner shown, the locking hook 27 may be supported separately from the slider 17 and may be made to engage the slider by means of stops.

In the shown preferred embodiment of the pincers 1, not only is the tube 2 detachable from the terminal structure 3, but the tube 2 is also rotatable relative to the terminal structure 3. For that purpose, the end segment 15 of the tube 2 is rotatably supported by its end-face borehole 24 on a corresponding cylindrical external surface of the terminal structure 3. The locking hook 27 is designed to engage the undercut groove 26 in any angular position. Furthermore, at least two drive surfaces 28 are present at the external circumference of the tube's end segment 15 and can be acted on to rotate the tube 2 relative to the terminal structure 3.

In the shown and preferred embodiment, the slider 17 exhibits a rectangular cross-section so that its elongated slot 18 will always point toward the rod 8.

In accordance with a second embodiment, the elongated slot 18 of the slider 17 subtends a passage in another manner. More specifically, a gripping zone is provided relatively away from the elongated slot in a direction of displacement of the slider 17.

Figure 3:
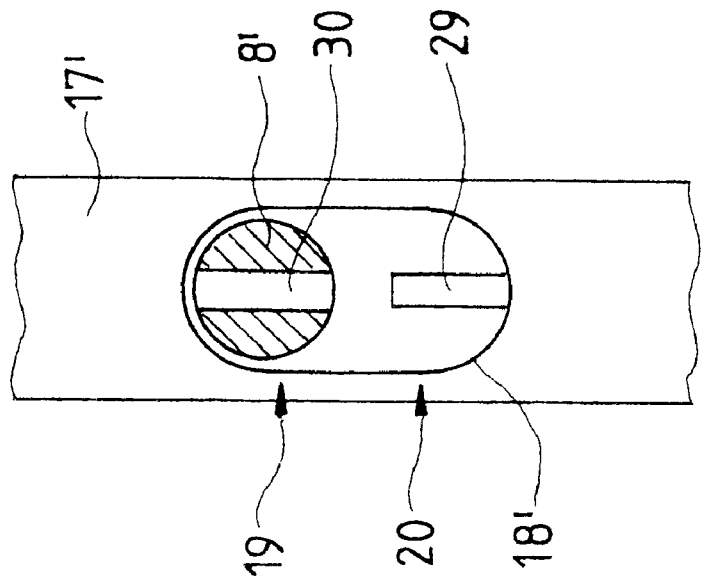

With reference to FIG. 3, a slider 17' is shown in an elongated slot 18' in the passage zone 19, which is exactly the same as in FIG. 2. While exhibiting again a large width of aperture in its gripping zone 20, the slider 17' has, on the other hand, a pin 29 that projects in the direction of displacement of the slider into the elongated slot 18'. In this design the rod 8' differs in its engagement zone 21 from that of the rod 8 of the first embodiment shown in FIGS. 1 and 2. The rod 8' has a circular cross-section and is fitted with a longitudinal slot 30 which the pin 29 fits into to secure the rod 8' against rotation. However, the rod 8' is axially displaceable when the pin 29 is received in the slot 30 while the rod 8' is situated in the gripping zone 20. Further embodiment modes are feasible.

What is claimed:

1. Pincers (1) for endoscopy surgery, comprising a terminal structure (3) to which is affixed a proximal end segment (15) of a tube (2) constituting a stem of the pincers, further a stationary handle (14) affixed to the terminal structure (3) and a displaceable handle (12) which rests on said stationary handle and which is fitted on an axis of the tube (2) at a proximal side of the terminal structure (3) with a swivel seat (11), further comprising a pincers head (4) which bears pincer arms (9) and which is both rotatably connected to the distal end of the tube (2) and is axially connected to it in detachable, geometrically locking manner (6, 7), further comprising a rod (8) which drives the pincers arms (9) and which in the pincers' assembled state runs through the tube (2) and detachably rests by its distal end in the swivel seat (11), further comprising an axially clear rotary connection (16, 18) between the rod (8) and the tube (2) in the proximal end segment (15) of the tube (2), wherein, in the pincers' assembled state, the rod (8), when being in the region of the rotary connection (16, 18), will exhibit at least one engagement zone (21) having an axially parallel, rotationally asymmetric cross-section, and in that a slider (17) rests in a transverse clearance (16) of the tube (2), said slider being fitted with an elongated slot (18) which admits and passes the rod (8) and which, in a passage zone (19), freely passes a maximum-diameter circular cross-section of the proximal segment of the rod (8) and which, in a gripping zone (20) that is offset in a sliding direction, encloses in an irrotationally locking manner the engagement zone (21) of the rod (8).

2. The pincers as claimed in claim 1, wherein the tube (2) is detachably affixed to the terminal structure (3) and secured by a locking device (26, 27), said locking device (26, 27) being connected to the slider (17).

3. The pincers as claimed in claim 1, wherein the tube (2) is rotatably affixed to the terminal structure.

4. The pincers as claimed in claim 1, wherein the slider (17) is guided in an irrotational manner in a borehole (16).

5. The pincers as claimed in claim 1, wherein the slider (17) is held by a spring (23) in the engaged position of the gripping zone (20) against the rod (8).

* * * * *